United States Patent
Sutton et al.

(10) Patent No.: US 6,936,727 B2
(45) Date of Patent: Aug. 30, 2005

(54) PROCESS FOR THE PRODUCTION OF ETHERS, TYPICALLY THF

(75) Inventors: David Mark Sutton, Kingston Upon Thames (GB); Andrew George Hiles, Chesham Bois (GB); Graham Reed, London (GB); John Anthony Stannard, London (GB)

(73) Assignee: Davy Process Technology Limited, London (GB)

( * ) Notice: Subject to any disclaimer, the term of this patent is extended or adjusted under 35 U.S.C. 154(b) by 1 day.

(21) Appl. No.: 10/483,524

(22) PCT Filed: Jul. 10, 2002

(86) PCT No.: PCT/GB02/03195

§ 371 (c)(1),
(2), (4) Date: Apr. 28, 2004

(87) PCT Pub. No.: WO03/006446

PCT Pub. Date: Jan. 23, 2003

(65) Prior Publication Data

US 2004/0199026 A1 Oct. 7, 2004

(30) Foreign Application Priority Data

Jul. 12, 2001 (GB) .............................................. 0117090

(51) Int. Cl.⁷ ............................................ C07D 307/08
(52) U.S. Cl. ........................................................ 549/508
(58) Field of Search ......................................... 549/508

(56) References Cited

U.S. PATENT DOCUMENTS

| | | | |
|---|---|---|---|
| 4,451,677 A | 5/1984 | Bradley et al. |
| 4,584,419 A | 4/1986 | Sharif et al. |
| 4,626,604 A | 12/1986 | Hiles et al. |
| 4,751,334 A | 6/1988 | Turner et al. |
| 4,767,869 A | 8/1988 | Harrison et al. |
| 4,795,824 A | 1/1989 | Kippax et al. |
| 4,919,765 A | 4/1990 | Wilkes et al. |
| 4,945,173 A | 7/1990 | Wood |
| 4,973,717 A | 11/1990 | Hiles et al. |
| 5,254,318 A | 10/1993 | Williams et al. |
| 5,310,954 A | 5/1994 | Hiles et al. |

FOREIGN PATENT DOCUMENTS

| | | |
|---|---|---|
| EP | 1 108 702 A1 | 6/2001 |
| GB | 1 226 292 A1 | 3/1971 |
| JP | 2001 048819 A1 | 2/2001 |
| WO | WO 86/03189 A1 | 6/1986 |
| WO | WO 88/00937 A1 | 2/1988 |
| WO | WO 90/08127 A1 | 7/1990 |
| WO | WO 91/01960 A1 | 2/1991 |
| WO | WO 91/01961 A1 | 2/1991 |
| WO | WO 91/01981 A1 | 2/1991 |
| WO | WO 97/43234 A1 | 11/1997 |
| WO | WO 97/43242 A1 | 11/1997 |
| WO | WO 99/48852 A1 | 9/1999 |

*Primary Examiner*—Bernard Dentz
(74) *Attorney, Agent, or Firm*—Davidson, Davidson & Kappel, LLC

(57) ABSTRACT

A process is described for the production of ethers, typically terahydrofuran, by reaction of a corresponding organic feed material selected from dicarboxylic acids and/or anhydrides, monoesters of dicarboxylic acids and/or anhydrides, diesters of dicarboxylic acids and/or anhydrides, lactones, and mixtures of two or more thereof in the presence of hydrogen which comprises the steps of: (a) supplying a stream comprising the organic feed material to a first vaporisation zone and contacting said feed with cycle gas comprising hydrogen such that at least a portion of the feed material is vaporised by and into the cycle gas; (b) supplying at least a portion of the cycle gas and the vaporised feed material to a first reaction zone comprising catalyst and operating under reaction conditions to allow hydrogenation and dehydration to occur; (c) recovering from the first reaction zone an intermediate product stream comprising unreacted feed material, cycle gas, desired product(s), and any co-products and by-products; (d) supplying the intermediate product stream to a second vaporisation zone and contacting it with additional feed material such that the said additional feed material is vaporised by and into the intermediate product stream; (e) supplying the product of step (d) to a subsequent reaction zone comprising catalyst and operating under reaction conditions to allow hydrogenation and, if required, dehydration to occur; and (f) recovering from the subsequent reaction zone a product stream comprising the ether.

15 Claims, 2 Drawing Sheets

PROCESS FOR THE PRODUCTION OF ETHERS, TYPICALLY THF

This application is a 371 of PCT/GB02/03195, filed Jul. 10, 2002.

BACKGROUND OF THE INVENTION

The present invention relates to the production of ethers, optionally with the co-production of diols and/or lactones by reaction of an organic feed material in the presence of hydrogen. The reaction will generally be by hydrogenation and/or dehydration. The organic feed material is selected from dicarboxylic acids and/or anhydrides, monoesters of dicarboxylic acids and/or anhydrides, diesters of dicarboxylic acids and/or anhydrides, lactones, a mixture thereof or a mixture of two or more thereof. In particular it relates to the production of $C_4$ to $C_{12}$ ethers, optionally with the co-production of the corresponding diols and/or lactones by the reaction of di-($C_1$ to $C_4$)alkyl esters of $C_4$ to $C_{12}$ dicarboxylic acids and/or anhydrides in the presence of hydrogen. More particularly, it relates to the production of cyclic ethers.

More particularly, the present invention relates to a process for the co-production of $C_4$ compounds, more specifically tetrahydrofuran, butane-1,4-diol and/or γ-butyrolactone from a hydrocarbon feedstock comprising a dialkyl maleate by vapour phase reaction in a hydrogen rich stream. In a particularly preferred arrangement of the present invention, it relates to a process for the production of at least 20% of tetrahydrofuran with co-production of butane-1,4-diol and/or γ-butyrolactone. In the most preferred arrangement it relates to the production of tetrahydrofuran with any residual butane-1,4-diol and/or γ-butyrolactone being recycled and converted to further tetrahydrofuran.

It is known to produce diols by hydrogenation of dialkyl esters of dicarboxylic acids and/or anhydrides, lactones, and mixtures thereof with a minor amount, typically no more than about 10 wt/wt % and preferably no more than 1 wt/wt %, of a monoester of the dicarboxylic acid and/or anhydride. Commercial plants have been built which produce butane-1,4-diol as the primary product with small amounts, typically up to about 10 mole %, of tetrahydrofuran and up to about 15 mole % of γ-butyrolactone by hydrogenation of a dialkyl ester of maleic acid and/or anhydride, such as dimethyl maleate or diethyl maleate, which may contain minor amounts of dialkyl fumarate and/or dialkyl succinate. Dimethyl succinate or diethyl succinate have also been suggested as suitable starting materials for hydrogenation to produce butane-1,4-diol, tetrahydrofuran and γ-butyrolactone. These succinates may be formed by any suitable manner and may be from biotechnology sources.

For further information regarding the operation of these plants reference may be made, for example, to U.S. Pat. Nos. 4,584,419, 4,751,334, WO-A-86/03189, WO-A-88/00937, U.S. Pat. Nos. 4,767,869, 4,945,173, 4,919,765, 5,254,758, 5,310,954 and WO-A-91/01960, the disclosure of each of which is herein incorporated by reference.

Whilst many plant operators aim to maximise the yield of butane-1,4-diol and to minimise the yield of the co-products, tetrahydrofuran and γ-butyrolactone, these co-products are themselves valuable commodity chemicals. The tetrahydrofuran is normally recovered as it is an important monomer for making elastomer fibres and is also an important solvent and therefore is a commercially important chemical. The γ-butyrolactone may be recovered but, as the market for this product is small, it is often recycled to the hydrogenation step for conversion to further butane-1,4-diol and the co-product tetrahydrofuran.

The dialkyl maleates which are used as feedstock in such hydrogenation processes may be produced by any suitable means. The hydrogenation of dialkyl maleates to yield butane-1,4-diol is discussed in detail in U.S. Pat. Nos. 4,584,419, 4,751,334 and WO-A-88/00937, which are incorporated herein by reference.

One conventional process for the production of butane-1,4-diol and co-product tetrahydrofuran with optional production of γ-butyrolactone is illustrated schematically in FIG. 1. In this process, a dialkyl ester, such as dimethyl maleate together with any residual methanol from the esterification reactor, is fed via line 1 to a vaporiser 2 where it is vaporised into a stream of hot cycle gas which is usually pre-heated. Cycle gas will normally contain a high concentration of hydrogen gas but may also include other gases including hydrocarbons, carbon oxides, methane, nitrogen. Further, where the cycle gas includes recycled gases from downstream, condensables including product ether, methanol, water, co-products and by-products may also be present.

The cycle gas is fed to the vaporiser 2 in line 3. The combined vaporous stream is then passed in line 4 to the reactor 5 where it is reacted to form butane-1,4-diol, tetrahydrofuran and/or γ-butyrolactone. The product stream 6 is cooled and the reaction products are condensed at 7 and separated from the cycle gas before being passed in line 8 to a refining zone 9. Recovered cycle gas is compressed and recycled in line 10. Make-up hydrogen will be added to the recovered cycle gas in line 11 with the enriched cycle gas being fed back to vaporiser 2. In the refining zone 9 the various products are separated and the butane-1,4-diol is removed in line 12 and the tetrahydrofuran in line 13. The γ-butyrolactone, together with the intermediate dimethyl succinate and some butane-1,4-diol may be recycled in lines 14 and 15. In one arrangement the γ-butyrolactone may be partially extracted in an optional refining zone 16 and removed in line 17. The methanol water stream separated from the product mix will be recycled upstream via line 18.

A significant portion of the butane-1,4-diol produced by this or other conventional methods is subsequently converted to tetrahydrofuran. This conversion step has substantial cost implications both in investment and operation of the plant required for the conversion and as the importance of tetrahydrofuran increases together with its use in derivative applications, it is desirable to provide a process for the production of tetrahydrofuran without the need for this expensive downstream processing. The downstream processing of conventional methods includes recovering the butane-1,4-diol, reacting it to form the tetrahydrofuran and then refining the tetrahydrofuran product.

In conventional processes, the quantity of cycle gas required to vaporise the feed is determined by a number of parameters including the operating pressure, the desired reaction temperature, the vaporiser exit temperature and the vapour pressure of the components to be vaporised.

Whilst it may be desirable to minimise the amount of cycle gas required, with prior art systems, this decrease will require the exit temperature from the vaporiser to be maintained high. However, maintaining a high vaporisation exit temperature would mean that the reaction temperature would be higher than desired. It is desirable to maintain the operating temperature as low as possible for several reasons including avoidance of hydrogen embrittlement of carbon steel equipment, avoidance of excessive catalyst deactivation and to minimise the formation of by-products such as butanol.

It will therefore be understood that the amount of cycle gas required for the reaction is determined by the vaporiser exit temperature and is therefore a compromise between the high temperature necessary to minimise the cycle gas required to vaporise the feed and the relatively low temperatures required for the reasons given above.

In the particular prior art system of the type illustrated in FIG. 1, in which the butane-1,4-diol is the main product, at a reactor inlet temperature of about 165° C. and a pressure of about 63 bar approximately 240 moles of cycle gas are required per mole of dimethyl maleate to be vaporised. Although the temperature will rise across the reactor, the reactor outlet stream will have about the same degree of saturation as the inlet stream because the vapour pressure of the butane-1,4-diol is less than that of the dimethyl maleate in the feed. Since the byproduct γ-butyrolactone and intermediate dimethyl succinate, together with the associated butane-1,4-diol are conventionally recycled to the reaction system, additional cycle gas is required to vaporise the recycle stream(s). This will typically increase the cycle gas requirements to about 310 mols of cycle gas per mole of the dimethyl maleate vaporised, which it will be understood is a significant increase.

Typically a process of the type illustrated in FIG. 1 will produce up to approximately 10 mole % tetrahydrofuran.

It is therefore desirable to provide a process for the production of higher mole % of tetrahydrofuran without the need for expensive downstream processing. It is further desirable to provide a process in which the cycle gas requirements are minimised such that investment and operating costs are reduced as the selectivity to tetrahydrofuran is increased.

SUMMARY OF THE INVENTION

Thus according to the present invention there is provided a process for the production of an ether by reaction of a corresponding organic feed material selected from dicarboxylic acids and/or anhydrides, monoesters of dicarboxylic acids and/or anhydrides, diesters of dicarboxylic acids and/or anhydrides, lactones, and mixtures of two or more thereof in the presence of hydrogen which comprises the steps of:
  (a) supplying a stream comprising the organic feed material to a first vaporisation zone and contacting said feed with cycle gas comprising hydrogen such that at least a portion of the feed material is vaporised by and into the cycle gas;
  (b) supplying at least a portion of the cycle gas and the vaporised feed material to a first reaction zone comprising catalyst and operating under reaction conditions to allow hydrogenation and dehydration to occur;
  (c) recovering from the first reaction zone an intermediate product stream comprising unreacted feed material, cycle gas, desired product(s), and any co-products and by-products;
  (d) supplying the intermediate product stream to a second vaporisation zone and contacting it with additional feed material such that the said additional feed material is vaporised by and into the intermediate product stream;
  (e) supplying the product of step (d) to a subsequent reaction zone comprising catalyst and operating under reaction conditions to allow hydrogenation and, if required, dehydration to occur; and
  (f) recovering from the subsequent reaction zone a product stream comprising the ether.

In the ether production reaction of the present invention, the conversion of the acid, anhydride and/or the lactone or ester to form the diol is an ester hydrogenation or hydrogenolysis and the reaction of the diol to the ether, is a dehydration reaction.

Without wishing to be bound by any theory, it is believed that the process of the present invention allows that the amount of product produced as light boiling (higher vapour pressure) ether rather than diol is increased, such that the outlet dewpoint of the reactor moves below the operating temperature such that further feed material can be vaporised into the stream until the stream approaches saturation. This is in marked contrast to conventional processes for the production of diols which the inlet and outlet of the reactor are close to the vapour dewpoint. The additional feed material vaporised by the process of the present invention may then be collected to product in the second reaction zone. By this means more feed may be processed to product than would have been possible with the conventional process unless the gas circulation rate was increased. In this connection it will be understood that a key factor in the cost of conventional processes relates to the hydrogenation loops which are themselves dependent on the amount of gas required to vaporise the feed; thus an increase of the gas circulation rate is particularly disadvantageous.

The cycle gas will normally contain a high concentration of hydrogen gas but may also include other gases including hydrocarbons, carbon oxides, methane, nitrogen. Further, where the cycle gas includes recycled gases from downstream, condensables including product ether, $C_1$ to $C_4$ alkanol, water, co-products and by-products may also be present In a particularly preferred embodiment of the present invention the ether is a cyclic ether. Most preferably the cyclic ether is tetrahydrofuran. In this latter case the organic feed material is preferably dialkyl maleate. Co-products which may be present to a greater or lesser extent in this embodiment or which may be absent include butane-1,4-diol and γ-butyrolactone. This reaction is illustrated in Scheme 1. In this example the alkanol is methanol and the intermediate material is partially hydrogenated dimethyl succinate.

By-products may include the alkanol used in the esterification of the acid or anhydride, for example methanol, undesirable material formed in side reactions, for example butanol, water evolved in the dehydration of the diol to the ether and intermediate material, for example dimethyl succinate together with other light or heavy materials formed in the process.

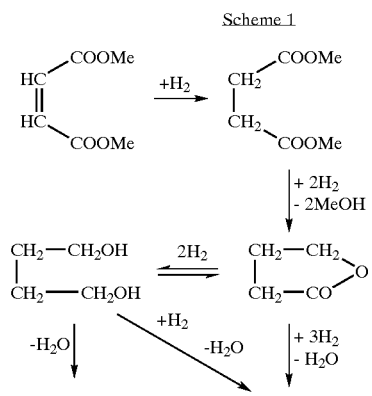

Scheme 1

-continued

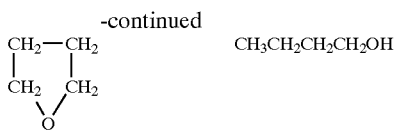    CH₃CH₂CH₂CH₂OH

The by-products may be separated from the ether in a refining zone and may be further purified if required. Similarly, the co-products may be separated from the ether in the refining zone and may be further purified if required.

However, in one arrangement, one or more of the co-products and/or by-products will be recycled to the first vaporisation zone where they will be vaporised. In one alternative arrangement, one or more of the co-products and/or by-products will be recycled to the second vaporisation zone where they will be vaporised into the intermediate product stream exiting from the first reaction zone.

Thus, in the preferred embodiment any dialkyl succinate present as a by-product may be recycled to one of the vaporisers, preferably the second vaporiser and hence to the corresponding reaction zone to improve the overall selectivity of the reaction to the desired tetrahydrofuran and co-products butane-1,4-diol and/or γ-butyrolactone.

The vapour pressure of tetrahydrofuran (8284 mmHg at 165° C.) is substantially higher than that of the butane-1,4-diol (76 mmHg at 165° C.), γ-butyrolactone (252 mmHg at 165° C.) and dimethyl maleate (262 mmHg at 165° C.). Thus, in the embodiment where tetrahydrofuran is produced, optionally with butane-1,4-diol and γ-butyrolactone, from dimethyl maleate as the conversion of feed dimethyl maleate to tetrahydrofuran is increased, the dew point of the exit stream from the first reaction zone is reduced. This allows for the additional feed and/or the or each optional recycle stream to be vaporised into the intermediate product stream from the first reaction zone.

Thus as the amount of ether, for example tetrahydrofuran, present in the intermediate product stream increases with improved selectivity, the capacity of the intermediate product stream to carry the additional organic feed, for example dimethyl maleate, and/or the recycle stream as a vapour is increased.

In the preferred embodiment of the present invention where dimethyl maleate is used in the formation of tetrahydrofuran, the cycle gas requirement is about 210 mols per mole of dimethyl maleate feed to the first reaction zone and additional cycle gas is not required to vaporise the recycle stream. Thus, if, for example, the catalyst in the first reaction zone gives approximately 50% selectivity to tetrahydrofuran then the total cycle gas required to vaporise both the feed and the recycle stream is reduced from about 310 moles required in the prior art process of FIG. 1 to about 210 moles per mole of dimethyl maleate. If in the preferred embodiment of approaching 100% selectivity for tetrahydrofuran is achieved, then about 100 to 110% more dimethyl maleate may be vaporised per mol of the cycle gas circulated compared with that achieved in the prior art process of FIG. 1, bringing the cycle gas requirement down to about 150 moles per mole of dimethyl maleate.

The capital cost of equipment and the operating cost of the reaction process, particularly energy and other utility requirements is largely determined by the cycle gas flow rate in the system. For example, the compressor, heat exchangers and interconnecting pipework are largely sized on the cycle gas flow rate and the power of compression and heat added to, and removed from, the reaction system are largely determined by the cycle gas flow. Thus increasing the conversion rate of the ester to ether allows that more moles of feed can be vaporised and hence more product made per mole of gas circulated which will have the advantage of substantially decreasing the capital and operating costs.

Where all of the co-products, such as butane-1,4-diol and γ-butyrolactone, are recycled to the subsequent vaporisation zone to provide high, preferably total, conversion to the ether e.g. tetrahydrofuran, it will not be necessary to minimise the lactone, for example γ-butyrolactone, to diol, for example butane-1,4-diol, ratio in the reaction by operating at high pressure as is required in conventional processes for co-producing butane-1,4-diol as the main product, with tetrahydrofuran and a minor amount of γ-butyrolactone. Indeed, it may be desirable to operate at a lower reaction pressure and hence, higher γ-butyrolactone to butane-1,4-diol ratio than has been desirable heretofore. This is in part because the γ-butyrolactone has a higher vapour pressure than the butane-1,4-diol and therefore requires less moles of cycle gas for vaporisation, but more significantly the investment and operating costs are reduced as the reaction pressure is lowered.

The feed material to the, or each, vaporisation zone may be, or may include, one or more recycle streams. Fresh organic feed and refining recycle streams may be vaporised together or may be vaporised in separate parts of the or each vaporisation zone. This is particularly advantageous as it will minimise the risk of transesterification between the ester and the diol.

In one arrangement, all of the cycle gas and the organic feed fed to the first vaporisation zone (step a) is supplied to the first reaction zone (step b) with the remaining organic feed and refining recycles being vaporised (step d) into the intermediate product stream recovered from the first reaction zone (step c) to form the intermediate feed stream which is fed to the subsequent reaction zone (step d).

In a second alternative arrangement, the gaseous stream from the first vaporiser (step a) may be divided with a major portion, preferably from about 70% to about 80%, being supplied to the first reaction zone (step b) and a minor portion, preferably from about 20% to about 30%, by-passing the first reaction zone and being fed to the subsequent vaporisation zone, preferably one part of the subsequent vaporisation zone (step d), where it is further heated such that additional organic feed material can be vaporised into the cycle gas before yielding a hot secondary feed stream. Where the minor portion is fed to one part of the subsequent vaporisation zone, the intermediate product stream recovered from the first reaction zone (step c) is fed to a second part of the subsequent vaporisation zone (step d) into which the refining recycles are fed. The two streams from the two separate parts of the subseqent vaporisation zone are then mixed to yield the intermediate feed stream which is fed to the subsequent reaction zone (step e).

One advantage of this preferred embodiment is that the liquid additional organic feed, which may be or include an ester, is separate from the liquid refining recycles which contain diols and/or lactones, and is only mixed therewith in the vapour phase. This will minimise the contact time and hence the potential for transesterification and progressive chain length growth.

The feed material fed to the or each vaporisation zone may be wholly, or may include, one or more recycle streams Whilst the present invention has been described with particular reference to two reaction zones, in one arrangement of the present invention, the process includes more than two reaction zones. Where there are more than two reaction zones, corresponding vaporisation zones may be located between adjacent reaction zones. Vaporisation in these subsequent zones may be made directly into the intermediate product stream from the previous reaction zone or if required a supplementary stream of cycle gas which may comprise one or more of fresh organic feed, refining recycle material and hydrogen may be included. The organic feed recycle material and/or hydrogen if present may be heated.

The organic feed material is preferably selected from mono $C_1$ to $C_4$ alkyl esters of $C_4$ to $C_{12}$ dicarboxylic acids and/or anhydrides, di $C_1$ to $C_4$ alkyl esters of $C_4$ to $C_{12}$ dicarboxylic acids and/or anhydrides, lactones of $C_4$ to $C_{12}$ hydroxycarboxylic acids, and mixtures of two or more thereof.

For example, the organic feed material can be selected from mono $C_1$ to $C_4$ alkyl esters of $C_4$ dicarboxylic acids and/or anhydrides, di $C_1$ to $C_4$ alkyl esters of $C_4$ dicarboxylic acids and/or anhydrides, γ-butyrolactone, and mixtures of two or more thereof. A particularly preferred organic feed material may be selected from monomethyl maleate, monomethyl fumarate, monomethyl succinate, dimethyl maleate, dimethyl fumarate, dimethyl succinate, γ-butyrolactone, recycle γ-butyrolactone and/or butane-1,4-diol and mixtures of two or more thereof. Alternatively the organic feed material can be selected from monoethyl maleate, monoethyl fumarate, monoethyl succinate, diethyl maleate, diethyl fumarate, diethyl succinate, γ-butyrolactone, recycle γ-butyrolactone and/or butane-1,4-diol and mixtures of two or more thereof.

In one arrangement, the organic feed material fed to one or more of the vaporisation zones is contained within an organic solvent. Where the organic solvent is present, one or more of the vaporisation zones is operated such that the organic feed material is essentially separated from the organic solvent by cycle gas stripping.

Suitable organic solvents include: di-($C_1$ to $C_4$ alkyl) esters of alkyl dicarboxylic acids containing up to 13 carbon atoms; mono- and di-($C_{10}$ to $C_{18}$ alkyl)esters of maleic acid, fumaric acid, succinic acid and mixtures thereof; ($C_1$ to $C_4$ alkyl)esters of napthalenemonocarboxylic acids; tri-($C_1$ to $C_4$ alkyl)esters of aromatic tricarboxylic acids; di-($C_1$ to $C_4$ alkyl)esters of isophthalic acid; alkyl phthalates; and dimethyl sebecate.

The vaporous feed stream to the first reaction zone preferably has a hydrogen-containing cycle gas:condensable material molar ratio in the range of from about 50:1 to about 1000:1.

Typically the feed temperature to the first hydrogenation zone is from about 100° C. to about 300° C., more preferably from about 150° C. to about 250° C., while the feed pressure to the first reaction zone is typically from about 50 psia (about 346 kPa) to about 2000 psia (about 13790 kPa), for example, more preferably from about 450 psia (about 3103 kPa) to about 1000 psia (about 6895 kPa).

The hydrogenatable material is preferably supplied to the first reaction zone at a rate corresponding to a liquid hourly space velocity of from about 0.05 to about 5.0 $h^{-1}$.

If desired, the pressure and/or the temperature can be adjusted in any convenient manner between the first and subsequent reaction zones and/or between adjacent reaction zones where more than two reaction zones are present. The temperature may be adjusted by any suitable means including the use of a heat exchanger or exchangers.

The hydrogen make up gas used in the process of the present invention can be obtained by any conventional manner. Preferably it contains at least about 50 volume % up to about 99.99 volume % or more, e.g. from about 80 to about 99.9 volume %, of hydrogen. It may further contain one or more inert gases, such as nitrogen or methane. Conveniently the hydrogen make up gas is produced by pressure swing absorption so that the cycle gas molecular weight is minimised thereby reducing the power required for compression and circulation of the cycle gas.

Any suitable catalyst for the reaction may be selected. Whilst a mixture of catalysts may be used, for ease of reference the term "catalyst" will be used herein and will be understood to mean either a single catalyst or a mixture of two or more different catalysts. The catalyst used in the subsequent reaction zone may be different from that used in the first reaction zone. Where there are more than two reaction zones present, the catalyst used in the or each zone may be the same as or different from that used in the first and/or subsequent reaction zone.

In one arrangement, a bed comprising a variety of catalysts may be used. In one example, the bed may include a catalyst that is tolerant of residual feed acid content, one which is suitable to promote hydrogenation of the ester and another which promotes selectivity to the desired ether. Catalyst beds comprising more than one type of catalyst may comprise discrete layers of catalyst within the bed such that different types are separated or the different catalyst types may be admixed.

In a particularly preferred process the catalyst of the first reaction zone is selected from noble metal and/or copper-containing catalysts. Hence the catalyst of the first hydrogenation zone can be or include one or more of a palladium catalyst, a reduced copper chromite catalyst or a reduced copper containing catalyst. The same or a different catalyst may also be used in the subsequent and any additional reaction zones. In one arrangement, the catalyst in at least the subsequent reaction zone is, or includes, a copper-containing catalyst.

Examples of copper-containing catalysts include reduced copper oxide/zinc oxide catalysts, reduced manganese promoted copper catalysts, reduced copper chromite catalysts, and reduced promoted copper chromite catalysts.

One alternative catalyst for use in at least one of the reaction zones is a reduced manganese promoted copper catalyst.

When the or each catalyst is a copper-containing catalyst, the active catalytic species may be at least partially supported on a supporting material selected from chromia, zinc oxide, alumina, silica, silica-alumina, silicon carbide, zirconia, titania, carbon, or a mixture of two or more thereof, for example, a mixture of chromia and carbon.

In one preferred process of the present invention an acid tolerant catalyst such as a promoted copper chromite catalyst may be used in at least one of the reaction zones. A suitable promoted copper chromite catalyst is, for example, the catalyst sold as PG85/1 by Davy Process Technology Limited of The Technology Centre, Princeton Drive, Thornaby, Stockton-on-Tees, TS17 6PY, England.

A catalyst which is effective to hydrogenate the ester to diols and lactones such as a manganese promoted copper catalyst may also be used in at least one of the reaction zones. A suitable manganese promoted copper catalyst which exhibits superior conversion of a dialkyl ester under typical operating conditions used for catalyst PG85/1 is sold as DRD92/89A by Davy Process Technology Limited. A catalyst with a high selectivity to the desired ether under typical operating conditions is DRD92/89B which is also available from Davy Process Technology Limited.

Further details of suitable catalysts can be found in International Patent Application No. PCT/GB00/04758 which is incorporated herein by reference.

Typically the hydrogenatable material will contain from about 0.01 to about 1.0 wt/wt % or more, e.g. up to about 10 wt/wt %, but normally no more than about 2.0 wt/wt %, of acidic material.

The charge of catalyst in the first reaction zone is preferably sufficiently large to reduce the content of acidic material to less than about 0.005 wt/wt % in passage of the vaporous mixture therethrough.

The amount of catalyst used in each reaction zone may be the same or different. The catalyst charge in the first reaction zone may constitute from about 10% to about 70%, more usually about 20% to about 50%, of the total catalyst volume in the reaction zones. Similarly the catalyst of the subsequent reaction zone is typically in the range of from about 70% to about 10%, more usually about 20% to about 50%, of the total catalyst volume of the reaction zones.

The selected catalyst preferably converts the ester, preferably the dialkyl maleate, to the desired ether, preferably a cyclic ether most preferably tetrahydrofuran, at a selectivity of from about 20% to about 90% or more, most preferably, about 70% or more.

The product stream from the final reaction zone is preferably fed, preferably having been condensed, to a refining zone where the desired ether, preferably tetrahydrofuran, is separated as product. Any co-products, such as butane-1,4-diol and/or γ-butyrolactone, which may be present may be separated or may be recycled to the reaction system. Where there is more than one co-product, one or more may be separated and recovered and the remainder recycled.

In one arrangement where 100% conversion to ether, for example tetrahydrofuran, is desired all of the co-products, for example butane-1,4-diol and/or γ-butyrolactone, are recycled.

The ability to select suitable catalysts and adjust the recycling of co-products to the or each vaporisation zone allows the plant operator flexibility to select the amount of ether produced relative to the formation of the or each co-product.

Any alkanol derived from the organic feed, which will typically be a $C_1$ to $C_4$ alkanol and water in the crude product stream will preferably be condensed and separated in refining. The alkanol will conventionally be recycled to the esterification reactor in which the organic feed material is formed, if present. The refining system may include means, if required to separate the water from the alkanol. The refining system will usually include means to separate other by-products which may be recycled. An example of a by-product which may be recycled is an for example any intermediate material. Alternatively some or all of any by-products produced may be rejected as effluent. An example of a by-product which may be rejected is any mono-ol produced.

BRIEF DESCRIPTION OF THE DRAWINGS

The present invention will now be described, by way of example, with reference to the accompanying drawings in which.

DETAILED DESCRIPTION OF THE INVENTION

It will be understood by those skilled in the art that the drawings are diagrammatic and that further items of equipment such as reflux drums, pumps, vacuum pumps, compressors, gas recycle compressors, temperature sensors, pressure sensors, pressure relief valves, control valves, flow controllers, level controllers, holding tanks, storage tanks, and the like may be required in a commercial plant. The provision of such ancillary items of equipment forms no part of the present invention and is in accordance with conventional chemical engineering practice.

Whilst for convenience, the description and drawing implies separate heat exchange, vaporisation and reaction equipment, it will be understood that some or all of these may be included into a single vessel or each associated vaporisation zone and reaction zone may be contained within a single vessel.

The present invention will now be described with particular reference to the production of tetrahydrofuran by reaction of a feed of dimethyl maleate with hydrogen.

Figure 2:
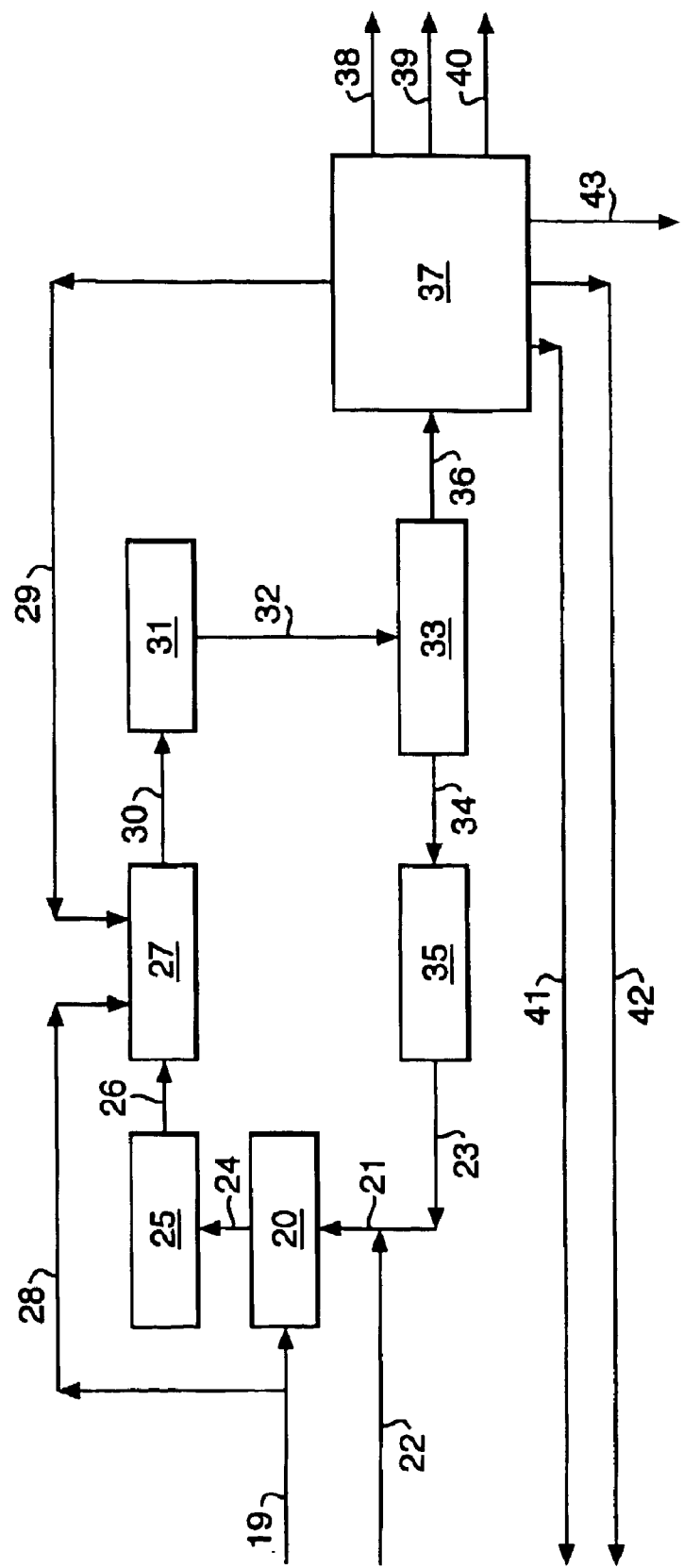
FIG. 2 is a schematic diagram of a process in accordance with the present invention.

FIG. 2 illustrates a plant for the production of tetrahydrofuran by reaction of dimethyl maleate with hydrogen in the vapour phase. The dimethyl maleate may be produced by any suitable means and may be supplied from an esterification plant (not shown) of the type described in WO-A-90/08127 which is incorporated herein by reference.

The resulting dimethyl maleate typically contains no more than about 10.0 wt/wt % of acidic organic materials, such as monomethyl maleate, and preferably less than about 2.0 wt/wt %, e.g. about 0.1 to about 1.0 wt/wt %, of acidic materials. The dimethyl maleate is fed in line 19 with a portion going to a first vaporisation zone 20 which may contain packing. The feed may be pumped to near the top of the vaporisation zone. The vaporisation zone is operated at a temperature of about 167° C. and a pressure of 900 psia (6205 kPa).

The feed flows down the vaporisation zone against an upflowing stream of cycle gas from line 21 which may include fresh make up hydrogen fed from line 22 that has been added to recovered cycle gas (line 23) from downstream. Alternatively, it may simply be the recovered cycle gas from line 23 with the makeup hydrogen may be added elsewhere in the system as convenient.

Where wetting of the catalyst may cause the catalyst to deteriorate it may be desirable to feed the reaction mixture to the reactor above the dew point. This can be achieved by either passing a suitable excess cycle gas flow through the vaporiser or adding extra cycle gas flow after the vaporiser, or adding extra heat to the reaction mixture before feeding to the reaction zone. However, if wetting of the catalyst is not deleterious to the operation of the catalyst, entrained liquid may be present. The reaction will, however, still be essentially a vapour phase reaction.

A near saturated vapour mixture stream comprising dimethyl maleate in cycle gas, with a cycle gas:dimethyl maleate molar ratio of about 150:1 is recovered from the top of the vaporisation zone.

The mixture of gases is then fed in line 24 to the first reaction zone 25 which contains a fixed bed catalyst charge.

The catalyst charge preferably contains acid tolerant catalyst such as PG85/1 and DRD92/89A which promote ester hydrogenation and DRD 92/89B which promotes diol dehydration. The reaction zone is generally operated at an inlet temperature of about 167° C. to about 175° C., an inlet pressure of about 900 psia (6205 kPa), and an exit temperature of about 195° C. The dimethyl maleate feed rate corresponds to a liquid hourly space velocity of 0.5 $h^{-1}$. Partial conversion of dimethyl maleate to butane-1,4-diol, tetrahydrofuran and γ-butyrolactone, as well as small quantities of undesirable by-products, such as butanol and/or acetal 2-(4'-hydroxybutoxy)-tetrahydrofuran, occurs in passage through reactor 25. In addition, partial hydrogenation of feed dimethyl maleate to dimethyl succinate occurs. The resulting first intermediate reaction mixture, passes through line 26 into the second vaporisation zone 27.

Fresh feed is added via line 28 and is mixed with the intermediate reaction mixture into which the fresh feed is vaporised. It may also be mixed with one or more recycled refining streams from downstream which are added in line 29. The hot intermediate reaction mixture will also vaporise the majority of the recycled material.

The mixture from vaporisation zone 27 is passed in line 30 to the second reaction zone 31, which contains a further charge of catalyst.

Here the further reaction is carried out and the amount of tetrahydrofuran in the product stream is increased. The product stream 32 is passed to a cooler and condenser 33 where the crude product is separated from the cycle gas which is recycled via a line 34 to a compressor 35 and lines 23 and 21 to the first vaporiser 20.

Crude product is passed in line 36 to a refining system 37. Here the crude product stream is separated, preferably by distillation in several stages, to yield pure tetrahydrofuran which is recovered in line 38. Lines 39 and 40 for the separate recovery of the butane-1,4-diol and the γ-butyrolactone may be provided or in a preferred arrangement, one or both of these, optionally together with partially hydrogenated feed material may be recycled in line 29 to the second vaporisation zone for further reaction to yield tetrahydrofuran.

Methanol and water may be recycled to upstream reactors in line 41 or may be separated and the methanol recycled in line 42 and the water extracted as effluent in line 43.

The invention will now be further described with reference to the accompanying examples.

COMPARATIVE EXAMPLE 1

Figure 1:
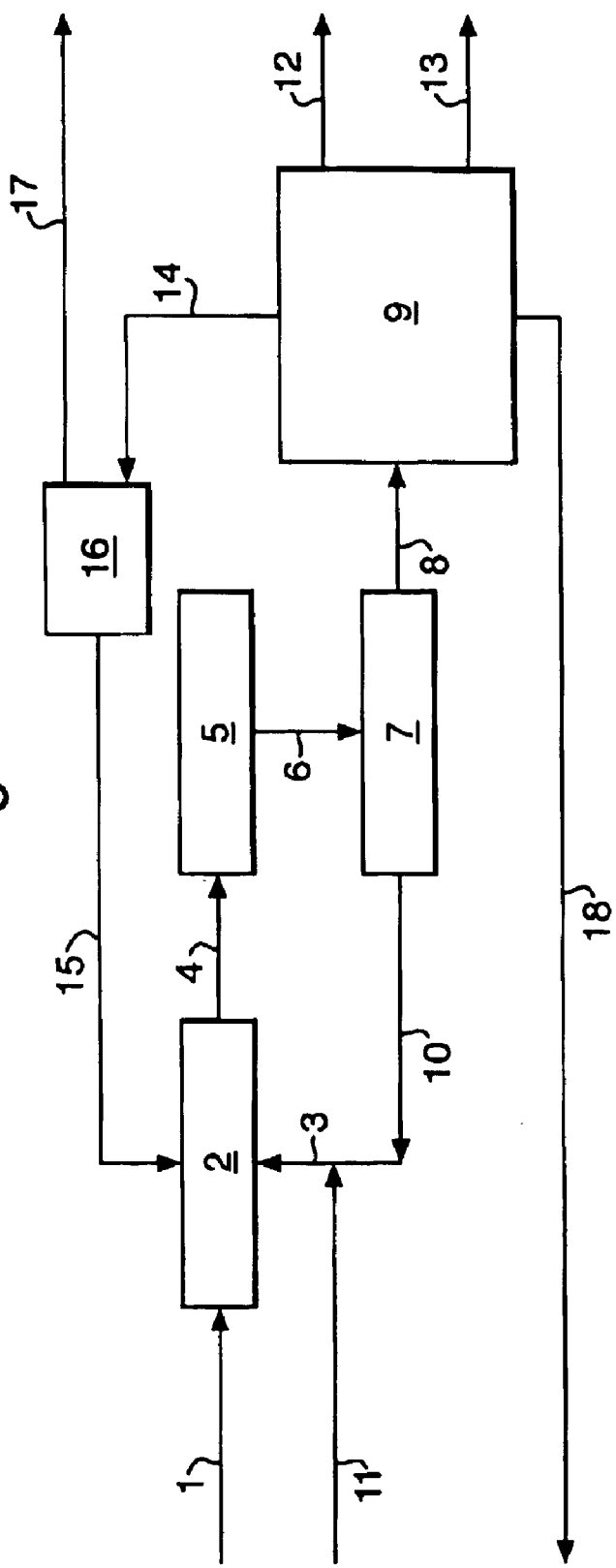
FIG. 1 is a schematic diagram of a prior art arrangement.

In a prior art process as illustrated in FIG. 1, in order to vaporise 1 kmol/h of which is fed to the vaporiser, 0.4 kmol/h of refining recycle, 311 kmol/h of hydrogen cycle gas and 4.9 kmol/h of make up hydrogen are also fed to the vaporiser. The vaporised stream is then fed via line 4 to the reactor where the dimethyl maleate and refining recycles are converted to crude reaction products. These are cooled and separated and the crude product is fed to a refining zone where the products are refined and the refining recycles are recycled to the vaporiser. The selectivity to tetrahydrofuran is measured. The reaction details and results are set out in Table 1.

EXAMPLE 1

In a process scheme in accordance with the present invention and as illustrated in FIG. 2, the compressor cycle gas stream is maintained at the same absolute rate as that for Comparative Example 1. In this arrangement, 1.5 kmol/h of dimethyl maleate is fed to the first vaporiser. No feed dimethyl maleate is fed to the second vaporiser. However, 0.3 kmol/h of refining recycle is fed to the second vaporiser. 311 kmol/h of hydrogen cycle gas and 7.6 kmol/h of make up hydrogen are fed to the first vaporiser to vaporise the dimethyl maleate feed and the vaporised stream passes to the first reactor where conversion to crude product occurs. The reactor contains a sufficient quantity of suitable catalyst to convert approximately 50% of the dimethyl maleate to tetrahydrofuran. The stream from this reactor passes to the second vaporiser where it is used to vaporise refining recycle. The stream from the second vaporiser passes to the second reactor where conversion to crude product occurs. The products from the second reactor are refined and the refining recycles separated and recycled to the second vaporiser. The selectivity to tetrahydrofuran is measured. The reaction details and results are set out in Table 1. It can be seen that approximately 50% more dimethyl maleate is reacted than is possible with the procedure of the prior art.

EXAMPLE 2

In a process scheme in accordance with the present invention and as illustrated in FIG. 2, the compressor cycle gas stream is maintained at the same absolute rate as that for Comparative Example 1. In this arrangement, a total dimethyl maleate feed of 1.9 kmol/h is fed to the system with 1.5 kmol/h being provided to the first vaporiser and 0.4 kmol/h to the second vaporiser. 311 kmol/h of hydrogen cycle gas and 9.4 kmol/h of make up hydrogen are fed to the first vaporiser to vaporise the dimethyl maleate feed before the vaporised stream is passed to the first reactor where conversion to crude product occurs. The reactor contains a sufficient quantity of suitable catalyst to convert approximately 50% of the dimethyl maleate to tetrahydrofuran. The stream from this reactor passes to the second vaporiser where it is used to vaporise refining recycle. The stream from the second vaporiser passes to the second reactor where conversion to crude product occurs. The products from the second reactor are refined and the refining recycles separated and recycled to the second vaporiser. The selectivity to tetrahydrofuran is measured. The reaction details and results are set out in Table 1. It can be seen that approximately 90% more dimethyl maleate is reacted than is possible with the procedure of the prior art.

EXAMPLE 3

In a process scheme in accordance with the present invention and as illustrated in FIG. 2, the compressor cycle gas stream is maintained at the same absolute rate as that for Comparative Example 1. In this arrangement, 1.5 kmol/h of dimethyl maleate is fed to the first vaporiser. No feed dimethyl maleate is fed to the second vaporiser. However, 0.75 kmol/h of refining recycle is fed to the second vaporiser 27. 311 kmol/h of hydrogen cycle gas and 7.6 kmol/h of make up hydrogen are fed to the first vaporiser to vaporise the dimethyl maleate feed before the vaporised stream passes to the first reactor where conversion to crude product occurs. The reactor contains a sufficient quantity of suitable catalyst to convert approximately 50% of the dimethyl maleate to tetrahydrofuran. The stream from this reactor passes to the second vaporiser where it is used to vaporise refining recycle. The stream from the second vaporiser passes to the second reactor where conversion to crude product occurs. The products from the second reactor are refined and the refining recycles separated and recycled to the second vaporiser. The selectivity to tetrahydrofuran is measured. The reaction details and results are set out in Table 1. It can be seen that approximately 110% more dimethyl maleate is reacted than is possible with the procedure of the prior art.

TABLE 1

|  |  | Comp. E.g. 1 | Example 1 | Example 2 | Example 3 |
|---|---|---|---|---|---|
| Vap1 DMM feed | kmol/h | 1.0 | 1.5 | 1.5 | 1.5 |
| Vap2 DMM Feed | kmol/h | N/A | 0 | 0.4 | 0.6 |
| Vap1 refining recycle | kmol/h | 0.4 | 0 | 0 | 0 |
| Vap2 refining recycle | kmol/h | N/A | 0.3 | 0.4 | 0.6 |
| Total DMM feed | kmol/h | 1.0 | 1.5 | 1.9 | 2.1 |
| Increase in DMM processed compared to Comp. e.g. 1 | % | N/A | 50 | 90 | 110 |
| Loop Pressure (exit final Reactor) | Bara | 62 | 62 | 62 | 62 |
| Vap1 Temp | °C. | 167 | 168 | 169 | 167 |
| Vap2 Temp | °C. | N/A | 192 | 187 | 182 |
| Make up Hydrogen | kmol/h | 4.9 | 7.6 | 9.4 | 11.0 |
| Cycle gas (at compressor) | kmol/h | 311 | 311 | 311 | 311 |
| Cycle gas/DMM feed | kmol/kmol | 311 | 211 | 167 | 148 |
| Reactor 1 THF selectivity | % | 2.8 | 47.4 | 47.4 | 90.0 |
| Overall THF selectivity | % | 2.8 | 47.0 | 47.0 | 61.8 |

Vap1 and Vap2 are the first and second vaporisers respectively.

Vap1 and Vap2 are the first second vaporisers respectively.

The dew points at various points in the first reaction zone are determined and compared. The results are set out in Table 2. These results assume that the hydrogenation reaction is 100% and is followed by dehydration. In reality it will be understood that some, i.e. less than 10 mol % dehydration may occur in the hydrogenation zone and that there will be some hydrogenation of residual ester and/or lactone in the dehydration zone. It is also necessary to note that the system is non-ideal and that it is necessary to allow for vapour pressure errors and heat of reaction errors.

TABLE 2

|  |  | Comp E.g. 1 | Example 1 | Example 2 | Example 3 |
|---|---|---|---|---|---|
| Reactor 1 Inlet Temp | °C. | 172 | 169 | 169 | 169 |
| Reactor 1 Inlet Dew Point | °C. | 161 | 164 | 164 | 164 |
| Reactor 1 Temp Exit - Hydrogenation Zone | °C. | 190 | 195 | 195 | 195 |
| Reactor 1 Dew Point Exit Hydrogenation Zone | °C. | 185 | 191 | 191 | 191 |
| Reactor 1 Temp Exit Dehydration Zone | °C. | — | 195 | 195 | 195 |
| Reactor 1 Dew Point Exit Dehydration Zone | °C. | — | 172 | 172 | 128 |
| Reactor 1 Exit Margin | °C. | 5 | 23 | 23 | 67 |

Thus it will be understood that Examples 1 to 3 have a significantly larger dew point margin exit for the first reactor than for the comparative example. This increase in dew point margin occurs primarily as a result of the dehydration of the butane-1,4-diol to the tetrahydrofuran that has taken place within the first reactor. It will be noted that the wider the dew point margin exit from the first reactor, the more feed material can be vaporised in the downstream vaporiser with a corresponding increase in hydrogenation loop productivity and reduction in the cycle gas flow per unit of dimethylmaleate feed.

What is claimed is:

1. A process for the production of an ether by reaction of a corresponding organic feed material selected from dicarboxylic acids and/or anhydrides, monoesters of dicarboxylic acids and/or anhydrides, diesters of dicarboxylic acids and/or anhydrides, lactones, and mixtures of two or more thereof in the presence of hydrogen which comprises the steps of:

(a) supplying a stream comprising the organic feed material to a first vaporization zone and contacting said feed with cycle gas comprising hydrogen such that at least a portion of the feed material is vaporized by and into the cycle gas;

(b) supplying at least a portion of the cycle gas and the vaporized feed material to a first reaction zone comprising catalyst and operating under reaction conditions to allow hydrogenation and dehydration to occur;

(c) recovering from the first reaction zone an intermediate product stream comprising unreacted feed material, cycle gas, desired product(s), and any co-products and by-products;

(d) supplying the intermediate product stream to a second vaporization zone and contacting it with additional feed material such that the said additional feed material is vaporized by and into the intermediate product stream;

(e) supplying the product of step (d) to a subsequent reaction zone comprising catalyst and operating under reaction conditions to allow hydrogenation and, if required, dehydration to occur; and (f) recovering from the subsequent reaction zone a product stream comprising the ether.

2. A process according to claim 1 wherein the cycle gas and vaporized organic feed from step (a) is divided with a major portion being supplied to step (b) and a minor portion to step (d).

3. A process according to claim 1 wherein all of the cycle gas and the vaporized feed material from step (a) is supplied to step (b).

4. A process according to claim 1 wherein the process additionally includes the step of separating any co-products and/or by-products from the product stream in a refining zone and recycling one or more of said co-products and/or by products in one or more recycle streams to one or more of the vaporisation zones where they will be vaporised.

5. A process according to claim 4 wherein the organic feed stream fed to at least one vaporization zone is, or includes, one or more recycle streams.

6. A process according to claim 1 wherein the process includes one or more additional subsequent reaction zones located in series between the first and final subsequent reaction zones and wherein the or each additional subsequent reaction zone is preceded by a vaporization zone in which additional feed, recycle or fresh feed and recycle are vaporized by and into the intermediate product stream from the previous reaction zone.

7. A process according to claim 1 wherein the recycle streams are vaporized into an intermediate product stream before being mixed with cycle gas comprising additional vaporized feed material.

8. A process according to claim 1 wherein the organic feed material is contained within an organic solvent which is separated from the feed material by cycle gas stripping in one or more of the vaporization zones.

9. A process according to claim 1 wherein the catalyst is a combination of different catalysts selected from high acid tolerance catalysts, high ester conversion hydrogenation catalysts and high ether formation catalysts.

10. A process according to claim 1, wherein the overall selectivity to the ether is more than 10%.

11. A process according to claim 1 wherein the selectivity to the ether is more than 30% in at least one reaction zone.

12. A process according to claim 1 wherein the organic feed material is selected from mono- $C_1$ to $C_4$ alkyl esters of $C_4$ to $C_{12}$ dicarboxylic acids and/or anhydrides, di- $C_1$ to $C_4$ alkyl esters of $C_4$ to $C_{12}$ dicarboxylic acids and/or anhydrides, lactones of $C_4$ to $C_{12}$ hydroxycarboxylic acids, and mixtures of two or more thereof.

13. A process according to claim 12 wherein the organic feed material is selected from monomethyl maleate, monomethyl fumarate, monomethyl succinate, dimethyl maleate, dimethyl fumarate, dimethyl succinate, y-butyrolactone, monoethyl maleate, monoethyl fumarate, monoethyl succinate, diethyl maleate, diethyl fumarate, diethyl succinate, y-butyrolactone, and mixtures of two or more thereof.

14. A process according to claim 1 wherein the ether is a cyclic ether.

15. A process according to claim 14 wherein the ether is tetrahydrofuran.

* * * * *